US008945007B2

(12) United States Patent
Ghevondian et al.

(10) Patent No.: US 8,945,007 B2
(45) Date of Patent: *Feb. 3, 2015

(54) PATIENT MONITOR

(75) Inventors: Nejhdeh Ghevondian, Eveleigh (AU); Hung Nguyen, Eveleigh (AU); Richard John Willshire, Eveleigh (AU)

(73) Assignee: University of Technology, Sydney, Sydney, New South Wales (AU)

( * ) Notice: Subject to any disclaimer, the term of this patent is extended or adjusted under 35 U.S.C. 154(b) by 1135 days.

This patent is subject to a terminal disclaimer.

(21) Appl. No.: 10/556,024

(22) PCT Filed: May 7, 2004

(86) PCT No.: PCT/AU2004/000599
§ 371 (c)(1),
(2), (4) Date: Apr. 5, 2006

(87) PCT Pub. No.: WO2004/098405
PCT Pub. Date: Nov. 18, 2004

(65) Prior Publication Data
US 2007/0060802 A1 Mar. 15, 2007

(30) Foreign Application Priority Data
May 8, 2003 (AU) ............................ 2003902187

(51) Int. Cl.
*A61B 5/00* (2006.01)
*G06F 19/00* (2011.01)
(Continued)

(52) U.S. Cl.
CPC .............. *A61B 5/6831* (2013.01); *G06F 19/34* (2013.01); *A61B 5/0002* (2013.01); *A61B 5/0205* (2013.01); *A61B 5/0402* (2013.01); *A61B 5/0531* (2013.01); *A61B 5/4806* (2013.01)
USPC ........................................................ 600/301

(58) Field of Classification Search
CPC ............ A61B 5/0452; A61B 5/14532; A61B 5/02405; A61B 5/7275; A61B 5/0022; A61B 5/02055; A61B 5/0006; A61B 5/04525; A61B 5/0456; A61B 5/6831; A61B 5/0002; A61B 5/0205; A61B 5/0402; A61B 5/531; A61B 5/4802; A61B 5/053–5/0538; A61B 5/08–5/0809; A61B 5/0295; A61B 5/0464–5/0468; G06F 19/3418; G06F 19/3406; G06F 19/3431; G06F 19/345; G06F 19/3468
USPC ......... 600/300–301, 383–384, 324, 481–528; 128/903–905, 920–925; 705/2–4; 340/573.1–576
See application file for complete search history.

(56) References Cited
U.S. PATENT DOCUMENTS 4,889,131 A 12/1989 Salem et al.
4,966,155 A 10/1990 Jackson
(Continued)

FOREIGN PATENT DOCUMENTS

EP 1127543 A1 2/2001
EP 1 092 453 A2 4/2001
(Continued)

OTHER PUBLICATIONS

Examiner's Report of Australian Government IP Australia on Oct. 19, 2009 regarding Patent Application No. 2004236368.
(Continued)

*Primary Examiner* — William Thomson
*Assistant Examiner* — Shirley Jian
(74) *Attorney, Agent, or Firm* — Perkins Coie LLP

(57) ABSTRACT

A monitoring device for monitoring the physiological condition of a patient (1) on a continuous basis, which includes a transmitter unit (2) adapted to attach to a patient so as to be in contact with the skin of a patient, a corresponding receiver unit (5). The transmitter unit includes a strap or belt (3) adapted to attach to or around a body part of a patient. A plurality of sensors (E) are mounted to the belt for monitoring a plurality of patient physiological parameters, including at least the patient's skin impedance, heart rate and aspects of the heart beat. The sensors are connected to a microcontroller (8) which processes the signals and which is linked to a wireless transmitter (9). A portable receiver unit is adapted to receive and process the signal from the transmitter. The receiver unit includes a display (14) for data relating to the patient and preferably an alarm (15).

23 Claims, 7 Drawing Sheets

(51) Int. Cl.
*A61B 5/0205* (2006.01)
*A61B 5/0402* (2006.01)
*A61B 5/053* (2006.01)

(56) References Cited

U.S. PATENT DOCUMENTS

| | | | |
|---|---|---|---|
| 5,437,285 A * | 8/1995 | Verrier et al. | 600/515 |
| 5,458,123 A | 10/1995 | Unger | |
| 5,464,021 A | 11/1995 | Birnbaum | |
| 5,507,288 A | 4/1996 | Böcker et al. | |
| 5,560,370 A * | 10/1996 | Verrier et al. | 600/518 |
| 5,670,944 A | 9/1997 | Myllymaki | |
| 5,842,997 A * | 12/1998 | Verrier et al. | 600/518 |
| 5,891,045 A * | 4/1999 | Albrecht et al. | 600/509 |
| 5,921,940 A * | 7/1999 | Verrier et al. | 600/518 |
| 6,047,206 A * | 4/2000 | Albrecht et al. | 600/509 |
| 6,416,471 B1 * | 7/2002 | Kumar et al. | 600/300 |
| 6,454,708 B1 * | 9/2002 | Ferguson et al. | 600/300 |
| 6,572,542 B1 * | 6/2003 | Houben et al. | 600/300 |
| 6,595,929 B2 * | 7/2003 | Stivoric et al. | 600/549 |
| 7,272,436 B2 * | 9/2007 | Gill et al. | 600/513 |
| 7,285,090 B2 * | 10/2007 | Stivoric et al. | 600/300 |
| 7,450,986 B2 * | 11/2008 | Nguyen et al. | 600/513 |
| 7,590,443 B2 * | 9/2009 | Bharmi | 600/509 |
| 8,002,700 B2 * | 8/2011 | Ferek-Petric et al. | 600/300 |
| 8,374,688 B2 * | 2/2013 | Libbus et al. | 600/547 |
| 2001/0034475 A1 | 10/2001 | Flach et al. | |
| 2001/0049471 A1 | 12/2001 | Suzuki et al. | |
| 2002/0019586 A1 * | 2/2002 | Teller et al. | 600/300 |
| 2002/0119586 A1 | 8/2002 | Kido | |
| 2004/0006279 A1 * | 1/2004 | Arad (Abboud) | 600/506 |
| 2004/0077962 A1 * | 4/2004 | Kroll | 600/513 |
| 2004/0167418 A1 * | 8/2004 | Nguyen et al. | 600/513 |
| 2006/0247685 A1 * | 11/2006 | Bharmi | 607/3 |

FOREIGN PATENT DOCUMENTS

| | | |
|---|---|---|
| EP | 1 127 543 A1 | 8/2001 |
| WO | WO 01/67950 A1 | 9/2001 |
| WO | WO 02/22010 A1 | 3/2002 |
| WO | WO-0222006 A1 | 3/2002 |
| WO | WO-02069798 A1 | 9/2002 |
| WO | WO-02078538 A2 | 10/2002 |

OTHER PUBLICATIONS

Examiner's Report of Australian Government IP Australia on Jun. 24, 2011 regarding Patent Application No. 2004236368.

* cited by examiner

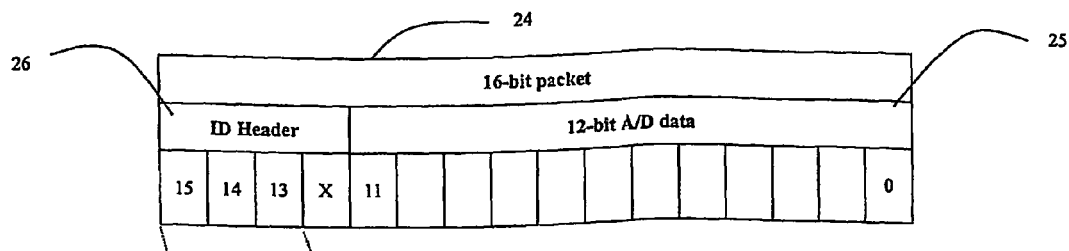
Figure 5a: Transmission Data Format
| 15 | 14 | 13 | ID bits Description | ID |
|----|----|----|---------------------|-----|
| 0 | 0 | 0 | Zero | Z |
| 0 | 0 | 1 | Skin imp. test circuit | SIt |
| 0 | 1 | 0 | Skin imp. short circuit | SIs |
| 0 | 1 | 1 | Skin impedance (gain = 1) | $SI_{G1}$ |
| 1 | 0 | 0 | Skin impedance (gain = 3) | $SI_{G3}$ |
| 1 | 0 | 1 | Skin impedance (gain = 10) | $SI_{G10}$ |
| 1 | 1 | 0 | Battery voltage | VBAT |
| 1 | 1 | 1 | ECG | ECG |
Figure 5b: Transmission Data ID Description
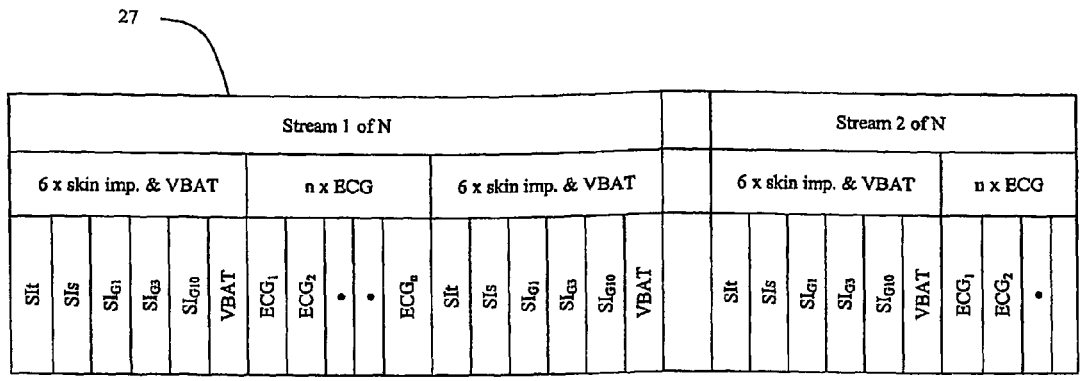
Figure 5c: Transmitter data sequence stream
FIG. 5

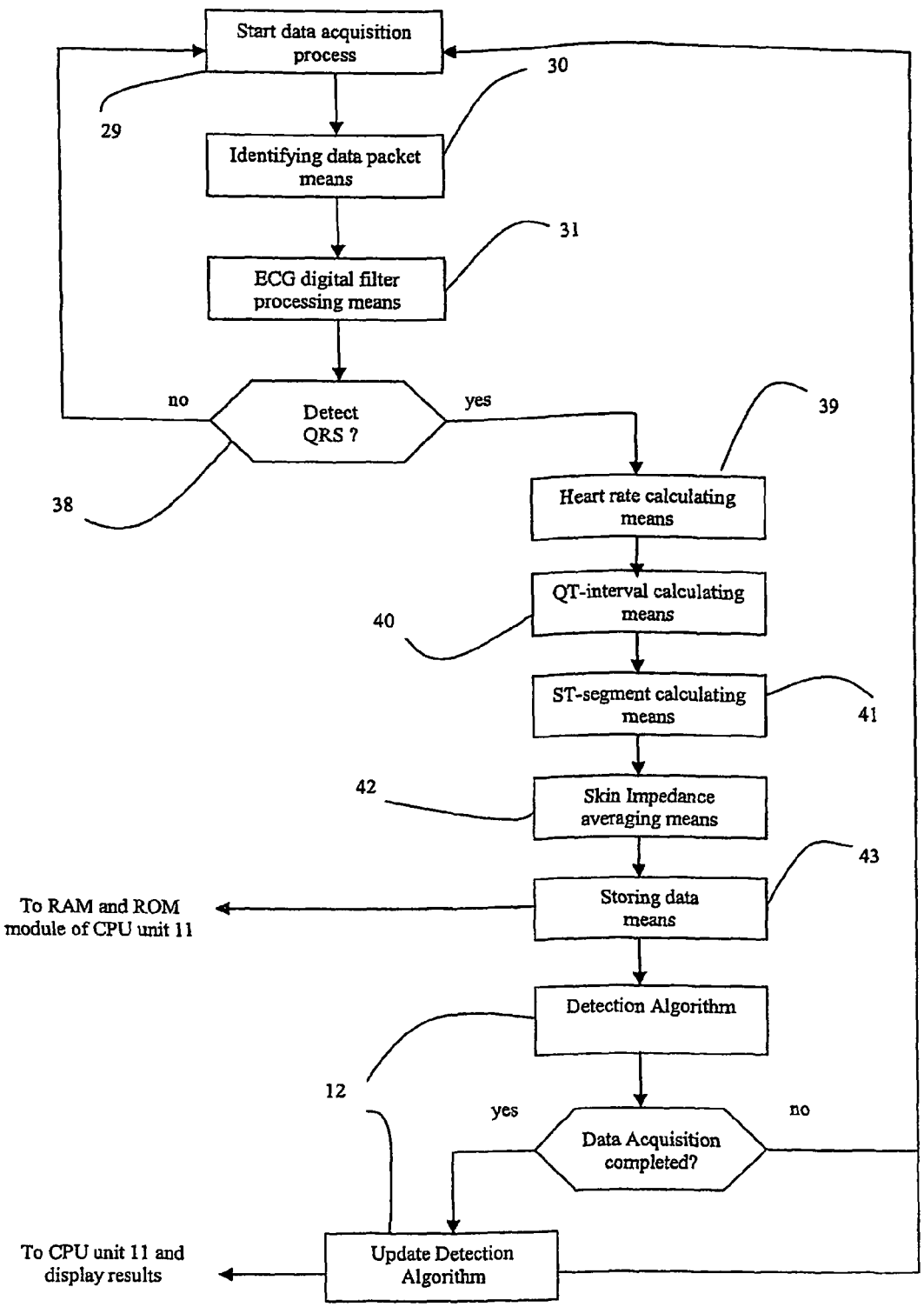
Figure 6a: Data acquisition process

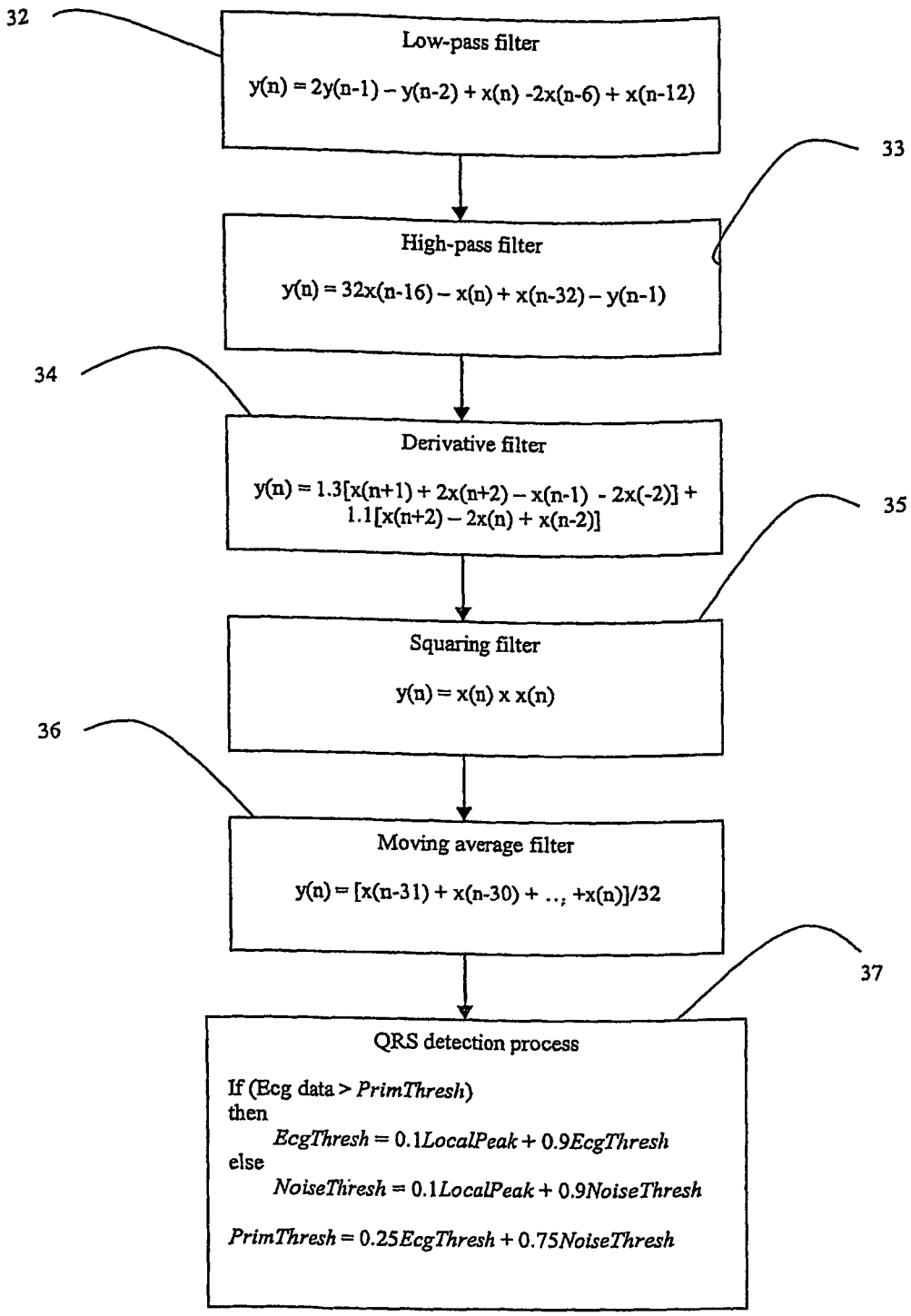
Figure 6b: ECG digital filtering process

PATIENT MONITOR

INTRODUCTION

This invention relates to a patient monitor, which is used in such a manner to monitor certain physiological conditions of a patient, and transmit the signals relating to these physiological conditions to a receiver unit, where the signals are processed to analyse and inform the patient/carer the severity status of the physiological condition.

More specifically the invention relates to a non-invasive method and apparatus for determining the onset of physiological conditions, such as, hypoglycaemia, hyperglycaemia, irregular blood glucose levels (BGL) and onset of fatigue.

BACKGROUND OF THE INVENTION

Earlier filed patent application (PCT/AU02/00218), relates to a non-invasive method and apparatus for determining onset of physiological conditions such as hypoglycaemia, irregular BGL, SIDS and the onset of fatigue.

As disclosed in the PCT application:

It is desirable with some physiological conditions to be able to monitor a patient in a non-invasive manner so that when a physiological condition presents itself, an alarm signal is triggered. The alarm activation will enable the patient to take remedial action or medication to prevent that physiological condition causing harm to the patient.

Certain physiological conditions, such as hypoglycaemia can be extremely dangerous and in many cases the symptoms can occur without the patient becoming aware of his/hers low BGL. The drop in BGL can occur reasonably fast, hence, a fast and accurate monitoring of low BGL hypoglycaemia) is essential, particularly, when the BGL is being monitored indirectly. The indirect BGL measurement methodology occurs by the monitoring of certain physiological parameters, including, skin impedance, heart rate, certain components of the electrocardiogram (such as QT interval) and their subsequent rate of change over the time.

It is also desirable that monitoring these physiological parameters cause minimal discomfort to the patient. Since many patients will require to monitor the physiological conditions for long periods of time (e.g. throughout the night), it is important that the monitoring system can be set up and used with minimum inconvenience and discomfort to the patient.

Prior art patent specifications have described various forms of belt or chest straps for monitoring certain physiological functions of the patient or user. For example one such belt is described and shown in U.S. Pat. No. 5,036,869, which uses chest belt with wireless telemetry system to transmit body signals from human body to a receiver. The body signals measured include electrode discharge detecting circuit, pacemaker signal detector, ECG and non-invasive sphygmomanometer (blood pressure measurement). These signals are then decoded and data processed by the receiver unit and interfaced to a generic measurement apparatus. The disclosed patent's claims are focused towards the telemetry platform of the system, and enhanced capability for measuring multiple body signals. Another patent described in U.S. Pat. No. 4,889,131 discloses a portable belt-type monitor which measures breathing and heart rate and produces an alarm signal when dysfunctions are detected. The alarm signals are then transmitted via wireless telemetry platform to a remote receiver unit. The core claims within this patent specification discuss the improved method of measuring ECG (or EKG) and respiration parameters. The claims also disclose a portable microcomputer system, with display, which can be attached to the described utility chest belt.

There are other chest-belt monitoring systems, including patents such as U.S. Pat. Nos. 5,464,021, 4,966,155, UK 2,291,505 and UK 2,368,645. In general, the devices and systems disclosed within these prior art specifications do not exhibit methodology and functionalities for detecting the early onset of certain physiological conditions. These prior art systems do not have the real-time analytical capabilities for detecting the onset of the physiological conditions.

SUMMARY OF THE INVENTION

According to the invention there is provided a monitoring device for monitoring the physiological condition of a patient on a continuous basis, the monitoring device comprising:

a transmitter unit adapted to attach to a patient so as to be in contact with the skin of a patient, the transmitter unit including:

attachment means adapted to attach to or around a body part of a patient;

a plurality of sensors mounted to the attachment means adapted to monitor a plurality of patient parameters, including at least the patients skin impedance, heart rate and aspects of the heart beat of the patient, the sensors adapted to each produce a signal related to the parameter being monitored;

a microcontroller to which the sensors are connected, the microcontroller being adapted to process the signals; and a wireless transmitter to which the microcontroller is connected, the transmitter being adapted to transmit a processed signal related to the physiological conditions monitored by the sensors;

a portable receiver unit adapted to receive and process the processed signal received from said attachment unit, the receiver unit comprising:

a wireless receiver adapted to receive the signal from the attachment unit;

a central processor adapted to further process and analyse the signal; and display means for displaying data relating to the patient.

Preferable the central processor is adapted to process the received processed signal so as to determine the onset of one or more of the following physiological conditions:

hypoglycaemia, irregular blood glucose levels, SIODS, cardiac irregularities, irregular BGL's, and onset of sleep/fatigue.

The portable receiver unit will preferable include communication means for communicating with a network. The receiver unit will preferably also include an input keyboard for inputting data and communicating with the receiver unit.

The transmitter unit preferably includes analogue electronics circuitry to pre-filter, process and prepare the signals related to the physiological conditions monitored by the sensors and interface to the microcontroller.

The microcontroller may be adapted to perform all required control mechanism for the transmitter unit, provide digital signal processing of the information by the pre-processed analogue circuitry and prepare these signals for wireless transmission.

The wireless transmitter to which the microcontroller is connected may be adapted to transmit the digitally processed signals related to the physiological conditions monitored by the sensors.

These and other features and advantages of the invention will be made apparent from the description of an embodiment thereof given below by way of example. In the description reference is made to the accompanying drawings, but the specific features shown in the drawings should not be construed as limiting on the invention.

BRIEF DESCRIPTION OF THE DRAWINGS

FIGS. 5a, 5b and 5c show the format of the packet stream transmitted by the chest-belt transmitter.

FIGS. 6a and 6b show the data acquisition process embedded within the central processing unit of the handheld receiver.

DETAILED DESCRIPTION OF THE EMBODIMENTS

Figure 1:
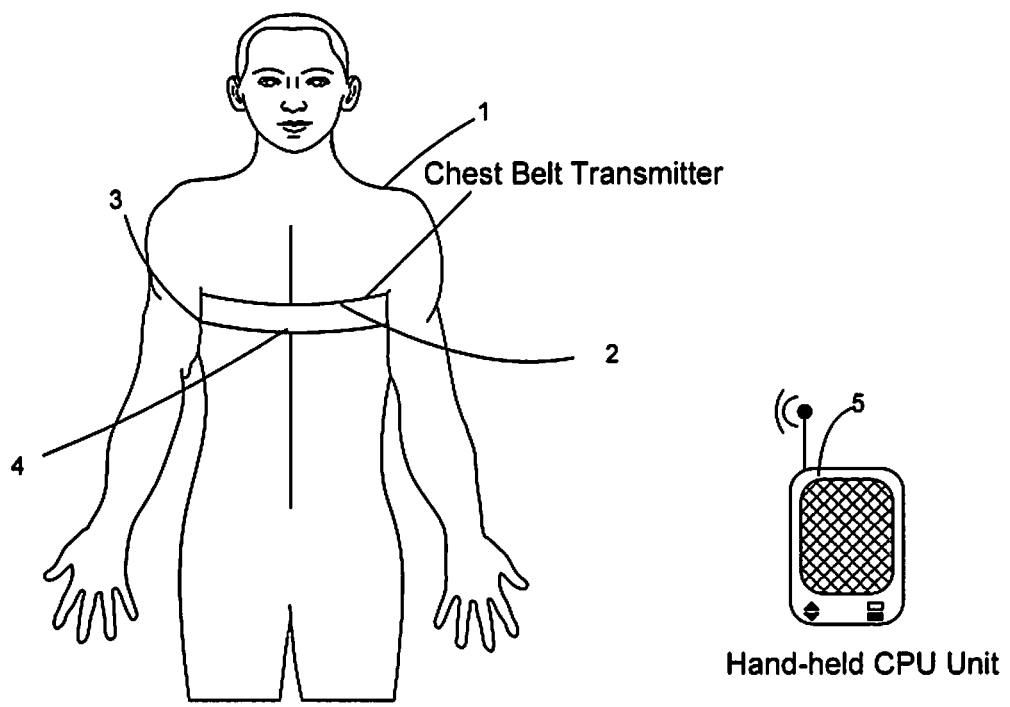
FIG. 1 shows a patient with a chest-belt transmitter together with a handheld processing unit formed in accordance with the present invention.

Referring to FIG. 1, a patient 1 as shown wearing a chest-belt unit 2 which is located around the patient in the upper thoracic region of the patient. The chest-belt unit 2 includes an adjustable elasticated strap 3 which is adapted to engage tightly around the patient's chest using a suitable and secure fastening system 6 which is relatively easy to engage and disengage to enable the belt unit 2 to be put on and taken off without difficulty. The strap unit 3 can also be adapted to fit around a child's chest in the same manner as the adult patient. The belt unit 2 incorporates an electronic housing 4 located in the centre of the belt unit 2, in front of the patient. The housing 4 includes, within its enclosure, a wireless transmitter, analogue electronic circuitry and a microcontroller, which will be described in more detail below.

Associated with the belt unit 2, is a hand-held receiver unit 5 which is adapted to process signals monitored by the unit 2 and transmitted to unit 5 by the transmitter unit located within the housing 4. The units 2 and 5 will be encoded to communicate only with each other.

Figure 2:
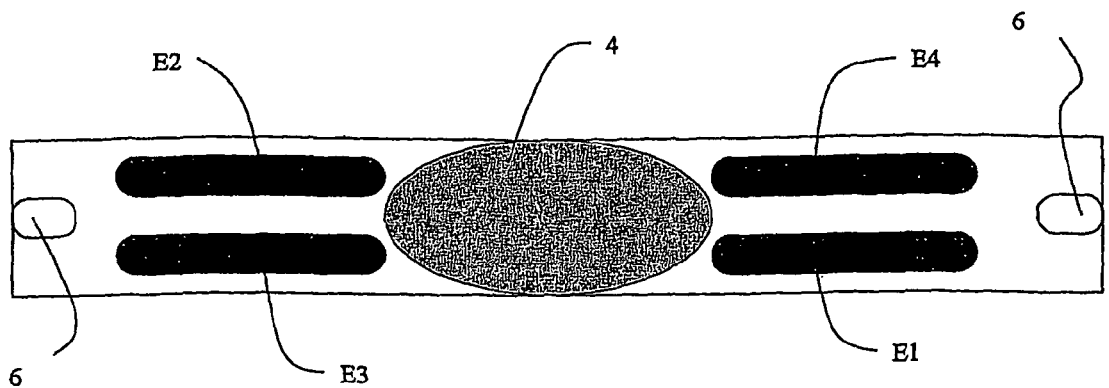
FIG. 2 shows a greater detail view of the chest-belt transmitter unit, including the sensors for use therewith.

As shown in FIG. 2, the belt unit 2 embeds four sensors which have been marked as E1, E2, E3 and E4 located on the underside thereof. These sensor units, E1 to E4, are in the form of skin surface electrodes and each of these sensors E1 to E4 is adapted to monitor a different patient physiological parameter. The sensors E1 to E4 will measure physiological parameters such as skin impedance, ECG and segments thereof, including QT-interval and ST-segment, heart rate and the mean peak frequency of the heart rate. These aspects are further discussed in detail in PCT/AU02/00218.

The sensors E1 to E4 are composed of a conductive polymer based material such as polypyrrole, having low impedance and low noise characteristics. These characteristics enable the sensors to measure ECG quality signals of the patient. These electrodes will also preferably be flexible so that the belt unit 2 will fit uniformly across the chest of the patient, and the electrodes will conform to contours of the chest, thereby ensuring quality contact at all times. The elasticity of the strap 3 will be such as to ensure proper contact of the electrodes with the user's skin.

Figure 3:
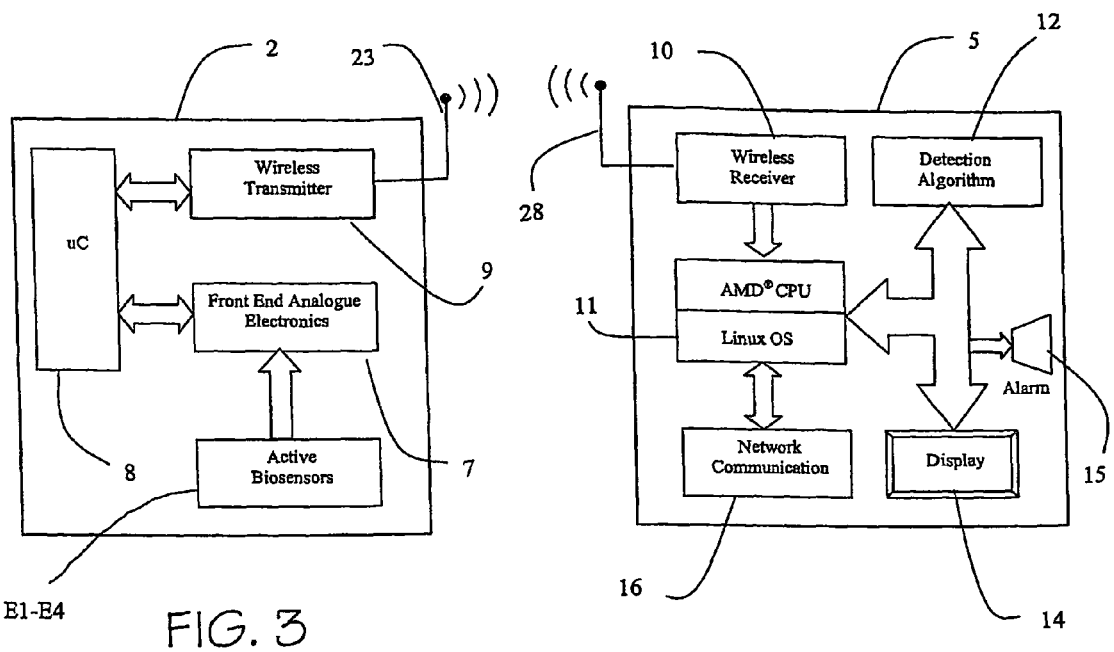
FIG. 3 shows in diagrammatic form the chest-belt transmitter and the handheld receiver unit according to the present invention.

As shown in the block diagram of FIG. 3, the electrodes E1-E4 provide the signals which interface to the front-end analogue electronics circuitry 7 in which they are processed, amplified, filtered and interface to the microcontroller (μC) unit 8. The μC unit 8 digitises the signals using an A/D (analogue-to-digital) converter and transmits the digitised signals via a wireless communication platform modulator 9 to the central receiver unit 5. In the unit 5, the received will be demodulated by a wireless receiver unit 10 and stored into the random access memory (RAM) of a central processing unit (CPU) 11. A blood glucose monitoring, hypoglycaemia and other physiological conditions detection algorithm 12 will then be used to calculate and estimate the onset of these conditions. The manner in which this is done is described in detail in the prior patent application PCT/AU02/00218. The resulting data will then de displayed in a display unit 14. The data can also be used to trigger an alarm system 15 to inform the patient or his or her carer as to the status relating to his or her physiological condition. In addition, the central receiver unit 5 includes a network communication port 16 with which the patient can communicate information relating to his or her physiological condition to a medical practitioner such as an endocrinologist or cardiologist.

Figure 4:
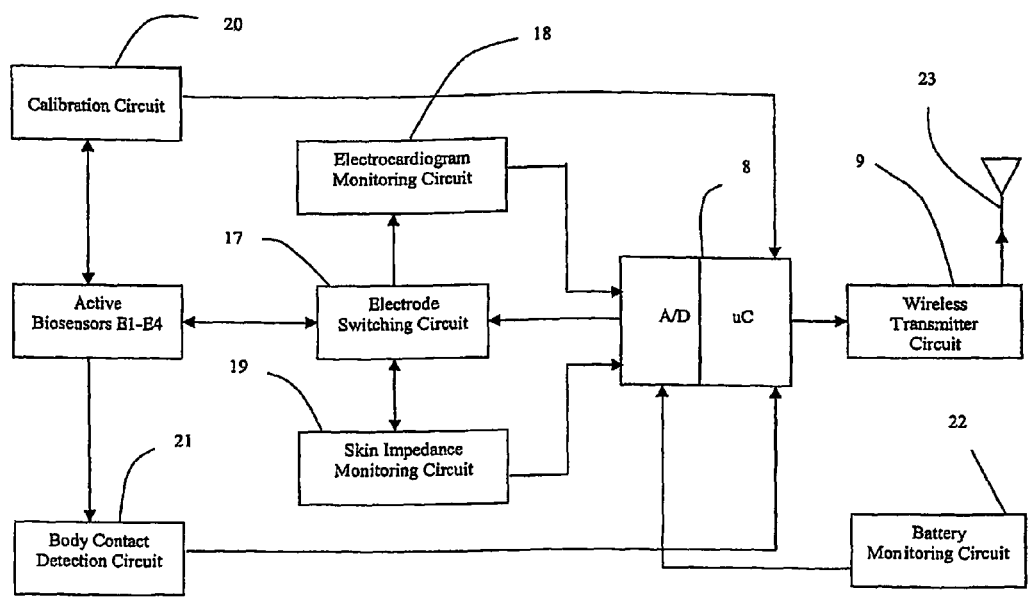
FIG. 4 shows the detailed functional block diagram of the chest-belt transmitter unit.

FIG. 4 shows the detailed function operation of the belt unit 2. The electrodes E1-E4 are multiplexed and shared to measure the physiological parameters such as the ECG and skin impedance. Hence, these electrodes are interfaced and controlled by an electrode switching circuit 17. This circuit unit 17 determines which physiological parameter is to be measured and directs the signal to the appropriate monitoring circuit, i.e. either the ECG monitoring circuit 18 or skin impedance monitoring circuit 19. The actual switching timetable will be pre-programmed and stored within the μC unit 8.

The ECG signal output from the monitoring circuit 18 is amplified, filtered within the ECG signal bandwidth of 150 Hz and interfaced to the A/D component of the μC unit 8. The skin impedance circuit 19 uses a variable frequency constant-current sinusoidal signal that is directed to one of the electrodes and the resulting voltage measured represents the skin impedance of the patient. The constant-current signal by the unit 19 uses a frequency range between 1 kHz and 1 MHz with a current amplitude between 10 μA and 1 mA. The resulting voltage measured by the electrodes are amplified, filtered and rectified by the monitoring unit 19, and interfaced to the A/D component of the μC unit 8, represent a DC signal representing the skin impedance of the patient. The monitoring circuit 19 also incorporates a gain switching circuitry which provides the amplification of skin impedance using three gain settings, i.e. gain of 1, 3 and 10. The A/D circuit within the μC unit 8 digitises the physiological signals into a 12-bit digital signal and stores these signals appropriately with the memory unit of 8.

The belt unit 2 consists of a body contact detection circuit 21 which is used to monitor and detect the detachment of the belt unit 2 from the patient. A digital output signal from this detection unit 21 is interfaced to the μC unit 8, representing the status of contact of the belt unit 2. That is, a digital signal high ("1") indicates belt unit 2 in contact with patient, a digital signal low ("0") indicates lift-off from patient. The belt unit 2 also consists of a calibration circuit 20 used to calibrate the measured signals by the skin impedance circuitry 19. Prior to the measurement of each skin impedance parameter, the circuit 20 switches a known impedance source (test circuit with known resistance value) at the input to the sensors E1-E4, and measures the resulting calibration signals, via the monitoring circuit 19, and stores the signal values in the μC unit 8. During the measurement of actual skin impedance signals, the circuit 19 disables the known impedance and resumes normal operations. The calibration signals are then used to calculate the accuracy of the constant-current source and the measured actual skin impedance values by the following:

Skin impedance (test circuit) measured from output of circuit 19 (in volts)=$SI_t$ Skin impedance (actual) measured from output of circuit 19 (in volts)=$SI_a$ Known resistance value in test circuit (in ohms)=$R_t$ Constant-current source (calculated) $I_{const}=SI_t/R_t$ Therefore, $SI_a$ (in ohms)=$SI_a/I_{const}$ As shown in FIG. 5a, the stored digitised signals obtained by μC unit 8 from the circuit unit 18 (ECG signals), circuit unit 19 (skin impedance) and battery monitoring circuit 22 are compiled and tagged to form a 16-bit data packet 24. The format of this 16-bit packet is 24 comprises of 12-bit signal data 25 together with a 3-bit identification header 26. FIG. 5b provides the description for each of the 3-bit ID header 26. ID bit 000 represents a zero packet, bit 001 represents the skin impedance using the calibration unit 20 to obtain the $SI_t$ value, bit 010 represents skin impedance with zero impedance using unit 20, bit 011 represents measured skin impedance using gain of 1, bit 100 represents measured skin impedance using gain of 3, bit 101 represents measured skin impedance using gain of 10, bit 110 represents the amount of charge left in the battery of unit 2 and bit 111 represents an ECG value.

As shown in FIG. 5c, the μC unit 8 further formats the 16-bit packet 24 into a long data stream sequence 27, which will be transmitted by the transmitter unit 9 and consequently received by the receiver unit 10. The data stream 27 consists of five skin impedance values ($SI_t$, $SI_s$, $SI_{G1}$, $SI_{G3}$, $SI_{G10}$), single battery voltage level (VBAT) followed by 'n' number of ECG values. The value 'n' can be programmable by the μC unit 8, to read plurality of ECG values from 1 up to 4096 times. Following the completion of the ECG stream six further skin impedance and battery voltage measurements ($SI_t$, $SI_s$, $SI_{G1}$, $SI_{G3}$, $SI_{G10}$ and VBAT) are made and formatted to the data stream 27. The resulting data stream 27 is encoded into a bi-phase (Manchester code) format and transferred to the transmitter unit 9, where the encoded stream 27 is transmitted via the embedded antenna 23 within the belt unit 2. The sequence of transmitting the data stream 27 via the μC unit 2 and the transmitter unit 9 is repeated up to 'N' times, where the value 'N' is programmable by the μC unit 8, to process the stream 27 up to 4096 times. The resulting 'N' number of encoded data stream 27 is received by the hand-held unit 5, via the receiver antenna 28 and transferred to the wireless receiver unit 10. The receiver unit 10 demodulates the bi-phase data back to the original data stream 27 and transfers and stores the resulting data to the RAM of the CPU unit 11.

FIG. 6 outlines the data acquisition and processing implemented within the CPU unit 11, in order to carry out all functional operations of the device and provide information relating to the onset of physiological condition of a patient. In one embodiment, the CPU unit 11 includes a learning neural network programmed with a fast learning algorithm. The identifying data packet unit 30 breaks down the data stream 27 into the 12-bit parameter data values 25 according to the 3-bit identification header 26. The ECG data packets (bit 111 of packet) is applied to an ECG digital filter processor unit 31, to detect sub-components of ECG including the QT-interval, ST-segment, heart rate and the average heart rate intervals.

The ECG filter unit 31 is a six part process consisting of a low-pass filter (LPF) unit 32, high-pass filter (HPF) unit 33, derivative unit 34, squaring function unit 35, moving averaging unit 36 and the QRS detection unit 37. The raw ECG data is applied to the LPF unit 32, which produces a band-limited signal, filtered for signals above the cut-off frequency of 11 Hz with a processing delay of 6 samples. The output data stream from unit 32 is then applied to the HPF unit 33, which filters for signals below 5 Hz cut-off frequency, with a processing delay of 16 samples. The filtered data is differentiated by the derivative unit 34 (using summation of first and second derivative approach) to provide the QRS peak slope value against its entire frequency bandwidth. Following the differentiation, the ECG data is applied to a squaring function unit 35 to produce all positive valued data stream and amplifies the QRS complex of the data enabling enhanced detection of the QRS peak. The data stream is further filtered by the stream to a moving average window unit 36 to remove unwanted sideband signals of the stream and produce a uniform waveform feature. The moving average window uses a window size of 32 data samples to produce the filtered output. The final stage of the ECG filtering process is the QRS complex detection unit 37 which performs a QRS peak detection algorithm and stores the resulting values. These results, in the form of R-R interval (interval between two consecutive QRS complex peaks) are used by the heart rate processing unit 39 to calculate the real-time hear rate value. The detection unit 37 uses three continuously changing threshold levels, including PrimThresh, EcgThresh and NoiseThresh. If the filtered ECG data stream is greater than the PrimThresh then a QRS peak has been detected. The PrimThresh is updated by the combination of the EcgThresh and NoiseThresh values. If a QRS complex is detected then EcgThresh is updated, otherwise NoiseThresh is updated.

The data acquisition process decides whether a QRS complex has been detected using unit 38, if so then the process continues to perform heart rate, QT-interval, ST-segment and skin impedance averaging calculations. The process also stores the data into the ROM of CPU unit 11 and writes results to various text files. However, if no QRS complex was detected then the process continues back to the start of data acquisition unit 29 and the process restarts.

The QRS detection intervals (R-R intervals) obtained by the detection unit 37 is applied to heart rate calculating unit 39 to obtain the real-time and the average heart rate values. The calculating unit 39 decides whether the current R-R interval ($R-R_c$) falls between a lower and upper limit of the average for the 8 most recent R-R intervals ($R-R_{avg1}$). The $R-R_c$ must be within 0.8 $R-R_{avg1}$ and 1.2 $R-R_{avg1}$ to be accepted into the new R-R&gi stream, otherwise $R-R_c$ is stored into a backup R-R interval average stream ($R-R_{avg2}$) in case no QRS complex is found in 8 consecutive ECG streams. The resulting QRS intervals ($R-R_c$, $R-R_{avg1}$ and $R-R_{avg2}$) are converted to the equivalent heart rate values ($HR_c$, $HR_{avg1}$ and $HR_{avg2}$) according to formula: (1/R-R interval)×60. The heart rate values $HR_c$, $HR_{avg1}$ and $HR_{avg2}$, along with the rate-of-change of heart rate, dHR (difference between current heart rate $HR_c$ and previous heart rate $HR_{c\_prev}$) are stored in the RAM module of the CPU unit 11.

The data acquisition sequence following QRS detection is the calculations of the QT-interval and ST-segments of the ECG using processing units 40 and 41 respectively. The QT-interval is calculated using the vector length between the start point of the QRS complex and the end of the T wave. The intersection point between the final slope of the T wave and a variable threshold value marks the end of the T wave. The threshold value is 0.15 of the previous T wave value. The calculating unit 40 analyses the current QT-interval ($QT_c$) for acceptance, between the range of 0.85 and 1.15 of the average for the 8 most recent QT values, $QT_{avg}$. The QT-interval values, $QT_c$, $QT_{avg}$ and dQT (difference between current $QT_c$ and previous QT-interval $QT_{c\_prev}$) are stored in the RAM module and ROM module (as text files) of the CPU unit 11.

The ST-segment is calculated using the vector length between the end of the QRS complex and the start of the T wave. The intersection point between the first positive of the derivative of the ECG and a variable threshold level marks the beginning of the T wave. Similarly to the QT-interval, the calculating unit 41 observes the current ST-interval ($ST_c$) for acceptance between the range of 0.85 and 1.15 of the average for the 8 most recent ST-segment values, $ST_{avg}$. The ST-segment values, $ST_c$, $ST_{avg}$ and dST (difference between current $ST_c$ and previous ST-interval $ST_{c\_prev}$) are stored in the RAM and ROM module (as text files) of the CPU unit 11.

The skin impedance averaging process 42 provides a single absolute skin impedance value ($SI_{avg}$) based upon the average of all three gain settings, i.e. with gain setting of 1 ($SI_{G1}$), gain setting of 3 ($SI_{G3}$) and gain setting of 10 ($SI_{G10}$). The flow of the process 42 algorithm is as follows:

1. Obtain $SI_{G1}$ reference value.
2. Check the range of $SI_{G3}$. If $SI_{G3}$ falls between 0.8 and 1.2 of $SI_{G1}$, then divide $SI_{G3}$ by 3 and average the results with $SI_{G1}$.
3. Similarly, check the range of $SI_{G10}$. If $SG_{G10}$ falls between 0.8 and 1.2 of $SI_{G1}$, then divide $SI_{G10}$ by 10 and average the results with $SI_{G1}$ and $SI_{G3}$ to obtain $SI_{avg}$.
4. Convert the single $SI_{avg}$ measured in volts to absolute skin impedance in ohms by dividing by $I_{const}$.
5. Also store $SI_{avg}$ into a data stream containing the average for the 8 most recent $SI_{avg}$ values, denoted as $SI_{avg\_hist}$.

The skin impedance values $SI_{avg}$, $SI_{avg\_hist}$ and dSI (difference between the current $SI_{avg}$ and the previous skin impedance value $SI_{avg\_prev}$) are stored in the RAM and ROM module (as text files) of the CPU unit 11.

The completed parameter data sequence, comprising of heart rate adapt set [$HR_c$, $HR_{avg1}$, $HR_{avg2}$, dHR], QT-interval data set [$QT_c$, $QT_{avg}$, dQT], ST-segment data set [$ST_c$, $ST_{avg}$ and dST] and skin impedance data set [$SI_{avg}$, $SI_{avg\_hist}$ and dSI] is applied to the first stage of the detection algorithm unit 12 for updating and leaning phase (methodology is described in detail in the prior patent application PCT/AU02/00218). The data acquisition process is repeated through the loop, starting from processing unit 29 to the detection algorithm unit 12, until the entire data stream 27 has bee processed by the first stage algorithm unit 12 and stored within the RAM and ROM memory of the CPU unit 11. At the completion of the acquisition processing loop the accumulated parameter data sets are applied to the second-stage of the detection algorithm 12 for the real-time detection for the onset of a physiological condition. The detection algorithm 12 will output the results, via the CPU unit 12, to a display unit 14, the status and severity of the physiological condition.

Figure 7:
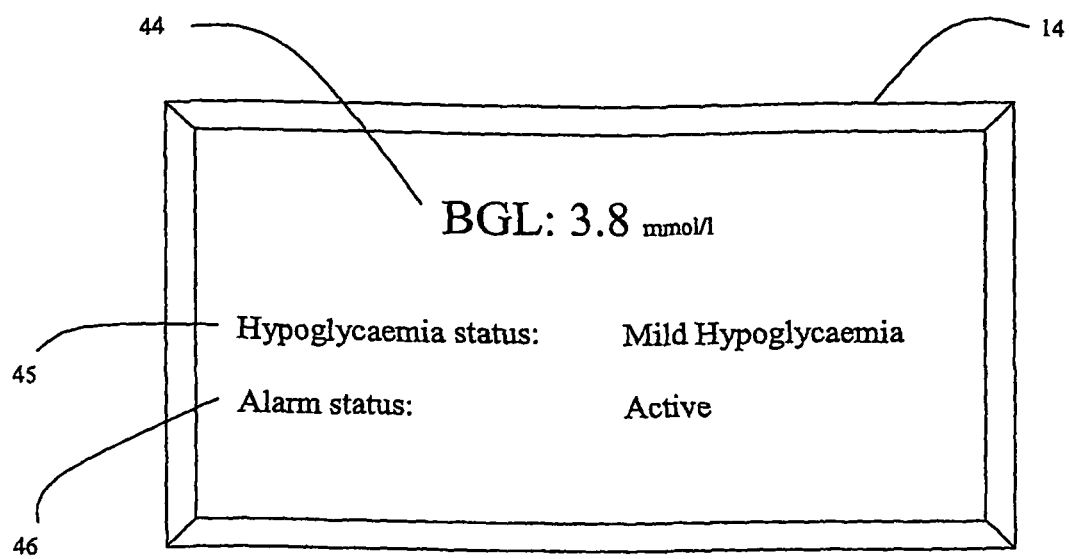
FIG. 7 shows the contents sample to be displayed in the display unit within the hand held receiver unit.

FIG. 7 shows a sample contents of information that may be displayed during an onset of a physiological condition (example data based on hypoglycaemia) on the display unit 14. The main physiological condition level is displayed as unit 44, informing the user in the form of absolute units. Display information 44 will also aid in administrating counter-regulatory action (by user or carer) against the onset of physiological condition. In the case for the onset of hypoglycaemia or hyperglycaemia, administration of glucose or insulin may be undertaken to counteract the onset and recover the patient to euglycaemia. In addition, information 44 may also be used in a control loop in conjunction to an automated control apparatus, such as an insulin-pump or an artificial pancreas, to automatically counter-regulate the physiological condition.

The display information 45 is used to inform the user/patient the status category of the physiological condition. Depending on the physiological condition, e.g. hypoglycaemia, the categories may include: normal, mild hypoglycaemia, mild-severe hypoglycaemia and severe hypoglycaemia. The display information 46 shows the status of the alarm activation, based on the severity of the physiological condition. There will be two states for the alarm information 46, i.e. active and inactive. When in active mode, a variable audio tone (a 'beep' usually 0.5 seconds in duration) is sent by the CPU unit 11 to the audio alarm unit 15 indicating the severity of the physiological condition. The following describes the rate of tone generated in case of hypoglycaemia:

Euglycaemia: Alarm inactive and no tone is generated

Mild hypoglycaemia: Alarm active, 'beep' every second is generated

Mild-severe hypoglycaemia: Alarm active, 2 'beep' every second is generated

Severe hypoglycaemia: Alarm active, 3 'beep' every second is generated

It will be understood that the present invention disclosed and defined herein extends to all alternative combinations of two or more of the individual features mentioned or evident from the text or drawings. All of these different combinations constitute various alternative aspects of the invention.

The foregoing describes embodiments of the present invention and modifications, obvious to those skilled in the art can be made thereto, without departing from the scope or spirit of the invention.

The invention claimed is:

1. A monitoring device for monitoring the hypoglycemic condition of a patient on a continuous basis, the monitoring device comprising:
   a transmitter unit adapted to attach to the patient so as to be in contact with the patient's skin, the transmitter unit including:
   attachment means adapted to attach to or around the chest of a patient;
   a plurality of sensors mounted to the attachment means to monitor a plurality of patient parameters while in contact with the skin, the monitored parameters including at least the patient's skin impedance and electrocardiogram (ECG), the sensors adapted to produce signals related to the parameters being monitored;
   a microcontroller to which the sensors are connected, the microcontroller multiplexing the sensors and processing the signals; and
   a wireless transmitter to which the microcontroller is connected to transmit a processed signal related to the patient parameters monitored by the sensors; and
   a portable receiver unit to receive and process the signal received from said wireless transmitter, the portable receiver unit comprising:
   a wireless receiver adapted to receive the signal from the wireless transmitter;
   a processor that processes the received signal to calculate sub-components of the patient's ECG including at least a heart rate and a QT interval, and wherein the processor determines the hypoglycemic condition of the patient based at least in part on the sub-components, wherein the processor includes a learning neural network processor programmed with a fast learning algorithm; and
   display means for displaying data relating to the hypoglycemic condition of the patient.

2. A monitoring device according to claim 1 wherein the portable receiver unit includes communication means for communicating with a network.

3. A monitoring device according to claim 1 wherein the portable receiver unit includes an input keyboard for inputting data and communicating with the receiver unit.

4. A monitoring device according to claim 1 wherein the transmitter unit includes analogue electronics circuitry to pre-filter, process and prepare the signals related to the patient parameters being monitored by the sensors and interface to the microcontroller.

5. A monitoring device according to claim 1 wherein the microcontroller controls the transmitter unit, provides digital signal processing of the information by the pre-processed analogue circuitry and prepares these signals for wireless transmission.

6. A monitoring device according to claim 1 wherein the microcontroller is adapted to output digitally processed signals related to the patient parameters monitored by the sensors.

7. A monitoring device according to claim 1 wherein the sensors comprise skin-surface electrode sensors comprised of flexible conductive polymer.

8. A monitoring device according to claim 1 wherein the transmitter unit is adapted to detect contact and lift-off of the sensors.

9. A monitoring device according to claim 1 wherein the processed signal transmitted by the transmitter unit comprises encoded packets of data including data relating to parameter identification.

10. A monitoring device according to claim 9 wherein the processor is adapted apply a digital signal processing algorithm to the packets of data.

11. A monitoring device according to claim 1 wherein the hypoglycemic condition is monitored by estimating a blood glucose level of the patient.

12. A monitoring device according claim 11 wherein the receiver unit is adapted to display the estimated blood glucose level of the patient.

13. A monitoring device according to claim 1 wherein the transmitter unit and receiver unit communicate across a plurality of radio frequency bandwidths.

14. A monitoring device according to claim 1 wherein the patient parameters are repeatedly monitored in sequence and the processed signal which is transmitted includes different components for the different parameters being monitored.

15. A system for monitoring a hypoglycemic condition of a patient on a continuous basis, the system comprising:
    a plurality of sensors that in use are held in contact with the skin of the patient, the sensors monitoring a plurality of patient parameters including the patient's skin impedance and electrocardiogram (ECG), the sensors producing signals related to the monitored patient parameters;
    attachment means adapted to attach to or around the patient's chest and hold the sensors in contact with the skin;
    a controller that multiplexes the plurality of sensors and processes the signals to provide skin impedance data and ECG data; and
    a processor that processes the ECG data to calculate sub-components of ECG including at least a heart rate and a QT interval and determine the hypoglycemic condition of the patient dependent on the skin impedance data and the calculated sub-components of ECG, wherein the processor includes a learning neural network processor programmed with a fast learning algorithm.

16. A system according to claim 15 comprising display means for displaying data relating to the hypoglycemic condition of the patient.

17. A system according to claim 15 wherein the processor comprises:
    means for detecting whether a QRS complex is present in the ECG data; and
    means for calculating the QT interval by determining a duration between a start point of the QRS complex and an end of a T wave in the ECG data.

18. A system according to claim 17 wherein the means for calculating the QT interval determines the end of the T wave as an intersection between a final slope of the T wave and a specified threshold value.

19. A system according to claim 18 wherein the means for calculating the QT interval specifies the threshold value as a function of a parameter of a preceding T wave in the patient's ECG data.

20. A system according to claim 17 wherein the means for detecting a QRS complex comprises:
    means for filtering the ECG data to provide a band-limited signal;
    means for differentiating the band-limited signal;
    means for squaring the differentiated signal;
    means for providing a moving average of the squared signal;
    means for detecting a QRS peak in the moving average dependent on a plurality of dynamically-varied threshold values ;and
    means for updating the threshold values.

21. A system according to claim 15 wherein the processor calculates sub-components of ECG selected from the set consisting of:
    heart rate;
    rate of change of heart rate;
    mean peak frequency of heart rate;
    QT interval;
    ST segment;
    a change in QT interval; and
    a change in ST segment.

22. A system according to claim 15 wherein the controller provides the ECG data to at least 12-bit resolution.

23. A system according to claim 15 wherein the controller comprises means for monitoring the patient's skin impedance using a plurality of gain values and the system comprises means for calculating an averaged skin impedance value based on the skin impedance data provided using the plurality of gain values, the detection means determining the hypoglycemic condition dependent on the averaged skin impedance value and the calculated sub-components of ECG.

* * * * *